United States Patent [19]

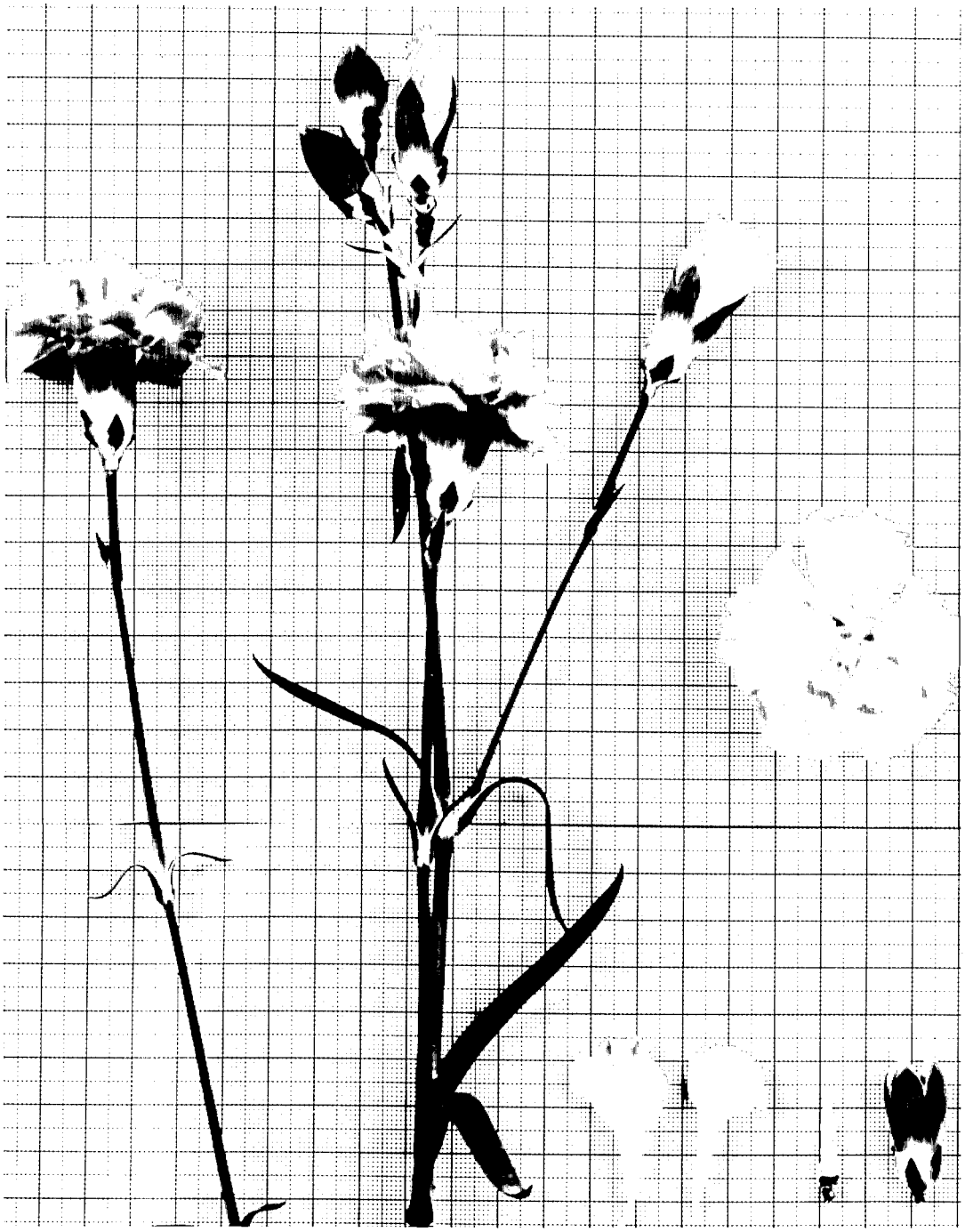

Hilverda

[11] Patent Number: Plant 5,574

[45] Date of Patent: Oct. 15, 1985

[54] CARNATION NAMED HILBAR

[75] Inventor: Jan J. Hilverda, Aalsmeer, Netherlands

[73] Assignee: Hilverda B.V., Aalsmeer, Netherlands

[21] Appl. No.: 559,360

[22] Filed: Dec. 8, 1983

[51] Int. Cl.[4] ..... A01H 5/00

[52] U.S. Cl. ..... Plt./72

[58] Field of Search ..... Plt./72

*Primary Examiner*—Robert E. Bagwill

*Attorney, Agent, or Firm*—Charles W. Rummler

[57] ABSTRACT

A new spray carnation cultivar having small pink flowers of a Cerise or Rose Bengal color which are produced continuously and profusely on tall, strong, flowering stems, distinguished by a vigorous and rapid growth rate reaching a height of about one meter.

1 Drawing Figure

BACKGROUND OF THE NEW PLANT

My new carnation cultivar originated as a seedling of unnamed parentage growing among a collection of carnations maintained particularly for breeding purposes at a commercial nursery at Aalsmeer, Holland. The crossing which produced this new plant was made by me in about 1979 with the object of developing new and better carnation varieties having a higher yield and improved quality. This new plant was discovered by me in about 1980 and selected for propagation and test because of its apparently rapid growth rate and its production of many very attractive button-sized blooms which appeared to be produced profusely. I propagated this plant by means of cuttings at Aalsmeer with such favorable results that I continued that kind of propagation through several successive generations, which demonstrated that its advantageous and novel characteristics would hold true from generation to generation and appeared to be firmly fixed.

DESCRIPTION OF THE DRAWING

My new variety of spray carnation is illustrated by the accompanying photographic drawing which shows, in full color, the upper portion of a typical spray stem bearing buds in various stages, together with fully opened flowers, the drawing also including a face view of a single fully opened flower and parts of a half opened bud to show the petal characteristics, the colors shown being as nearly true as it is reasonably possible to obtain by conventional photographic procedures.

DESCRIPTION OF THE NEW PLANT

The following is a detailed description of my new carnation plant based upon observations of greenhouse grown plants at Aalsmeer, Holland, in the Spring and Summer of 1983, the color designations being according to The R.H.S. Colour Chart published by The Royal Horticultural Society of London, England.

THE PLANT

Origin: Seedling.

Parentage: Selected unnamed seedlings from a carnation collection being grown and maintained for breeding purposes.

Classification:

*Botanic.*—*Dianthus caryophyllus.*

*Commercial.*—Greenhouse carnation.

Form: Bush of tall spray shape.

Height: Approximately one meter.

Growth habit: Quite rapid, vigorous, upright and strong.

Branching character: Alternate.

Foliage:

*Quantity.*—Abundant.

*Size of leaf.*—Approximately 10 to 12 cm. long.

*Shape.*—Sessile, lanceolated and with smooth margins.

*Texture.*—Leathery.

*Color.*—Upper side — Blue-Green. Under side — Blue-Green.

*Leaflets.*—None.

*Ribs and veins.*—The midrib is prominent.

THE BUD

Size: Medium.

*Diameter.*—About 12 to 15 mm.

*Length.*—About 20 to 30 mm.

Form: Oval shaped and pointed.

Rate of opening: From a mature bud, the flower will open about three days later.

Color:

*When sepals first divide.*—Dark Pink or Cerise.

*When petals begin to unfurl.*—Dark Pink of a Cerise or Rose Bengal color.

Sepals: Hooded over the bud and stand up when the flowers open.

*Shape.*—Generally ovate with blunt base and somewhat acuminate tip.

*Color.*—Inside — Light Green. Outside — Dark Green.

Calyx:

*Shape.*—Funnel-shaped.

*Size.*—Medium.

*Aspect.*—Smooth.

*Splitting.*—The calyx does not split.

Flower stem:

*Length.*—Approximately 50 cm.

*Character.*—Rigid and erect.

*Color.*—Dark Green.

THE FLOWER

Blooming habit: Profuse and continuous.

Size of bloom: Small.

*Diameter.*—Approximately 55 mm.

*Depth.*—Approximately 25 mm.

Borne: In cluster with more than three flowers per stem.

Shape: When bloom first opened, high centered. When bloom matures, it tends to flatten.

Petalage:

*Number of petals.*—26.

*Arrangement.*—Imbricated.

*Form.*—Folded with dentated margin.

*Texture.*—Soft.

*Appearance.*—Velvety.

*Color.*—All petals, top side and reverse side, R.H.S. 57C.

Petaloids:

*Number.*—26.

*Size.*—40 To 50 mm.

Flower stem:

*Length.*—About 50 to 60 cm.

*Character.*—Sturdy and upright.

*Color.*—Dark Green.

Persistence: The petals hang on and dry.

Fragrance: Weak.

Disease resistance: Resistant to fusarium oxysporum and fusarium redolens as observed in practice in The Netherlands.

Lasting quality:

*As a cut flower.*—10 to 14 days.

REPRODUCTIVE ORGANS

Stamens: Normal in number and arranged evenly.

*Anthers.*—Size: Normal. Color: Cream.

*Filaments.*—Length: 10 to 20 mm. Color: White.

Pistils:

*Number.*—Not more than three.

*Styles.*—Length: Approximately 20 mm. Color: White.

*Stigmas.*—Color: White with pinkish top.

Ovaries: Of cylindrical shape, and light green with white base.

*Aspect.*—Smooth and slightly ribbed.

The distinguishing characteristics of this particular carnation cultivar reside in its much faster growth and higher yield than normal with more vigorous and sturdy stems.

I claim:

1. The new and distinct spray carnation variety, substantially as herein shown and described, characterized by its continuous and profuse production of small pink flowers, and its rapid growth rate.

* * * * *

UNITED STATES PATENT AND TRADEMARK OFFICE

CERTIFICATE OF CORRECTION

PATENT NO. : Plant 5574

DATED : October 15, 1985

INVENTOR(S) : Jan J. Hilverda

It is certified that error appears in the above-identified patent and that said Letters Patent is hereby corrected as shown below:

Title of invention should read -- Carnation named Hilbacer --.

Signed and Sealed this

*Eighteenth* Day of *February 1986*

[SEAL]

*Attest:*

DONALD J. QUIGG

*Attesting Officer*

*Commissioner of Patents and Trademarks*